United States Patent [19]

Grassme

[11] Patent Number: 4,475,224
[45] Date of Patent: Oct. 2, 1984

[54] DENTAL X-RAY DIAGNOSTIC INSTALLATION

[75] Inventor: Ulrich Grassme, Nuremberg, Fed. Rep. of Germany

[73] Assignee: Siemens Aktiengesellschaft, Berlin & Munich, Fed. Rep. of Germany

[21] Appl. No.: 425,316

[22] Filed: Sep. 28, 1982

[30] Foreign Application Priority Data

Oct. 30, 1981 [DE] Fed. Rep. of Germany ....... 3143160

[51] Int. Cl.³ ............................................. G03B 41/16
[52] U.S. Cl. ...................................... 378/38; 378/108; 378/110; 378/112
[58] Field of Search ...................... 378/38, 39, 40, 108, 378/110, 112

[56] References Cited

U.S. PATENT DOCUMENTS 4,021,672  5/1977  Franke ................................ 250/402
4,333,012  6/1982  Furnichi .............................. 378/38

Primary Examiner—Craig E. Church

Attorney, Agent, or Firm—Hill, Van Santen, Steadman & Simpson

[57] ABSTRACT

A dental x-ray diagnostic installation has an exposure unit consisting of an x-ray tube and a cassette holder for generating a dental x-ray exposure. The exposure unit is rotatable about a patient's head by a motor. A radiation detector is attached to the cassette holder which supplies an electrical signal corresponding to the radiation dose rate to a dose rate regulator which in turn operates a voltage control unit which sets the level of high voltage supplied to the x-ray tube such that the dose rate of the radiation emitted by the x-ray tube is maintained at a value for producing an optimum film exposure. A range adjustment for the x-ray tube voltage is externally selected and limits operation of the voltage control unit such that if the dose rate regulator supplies a signal to the voltage control unit requiring a voltage which exceeds the set limit, the voltage control unit is inhibited and instead the motor speed is adjusted to maintain the optimum exposure.

4 Claims, 1 Drawing Figure

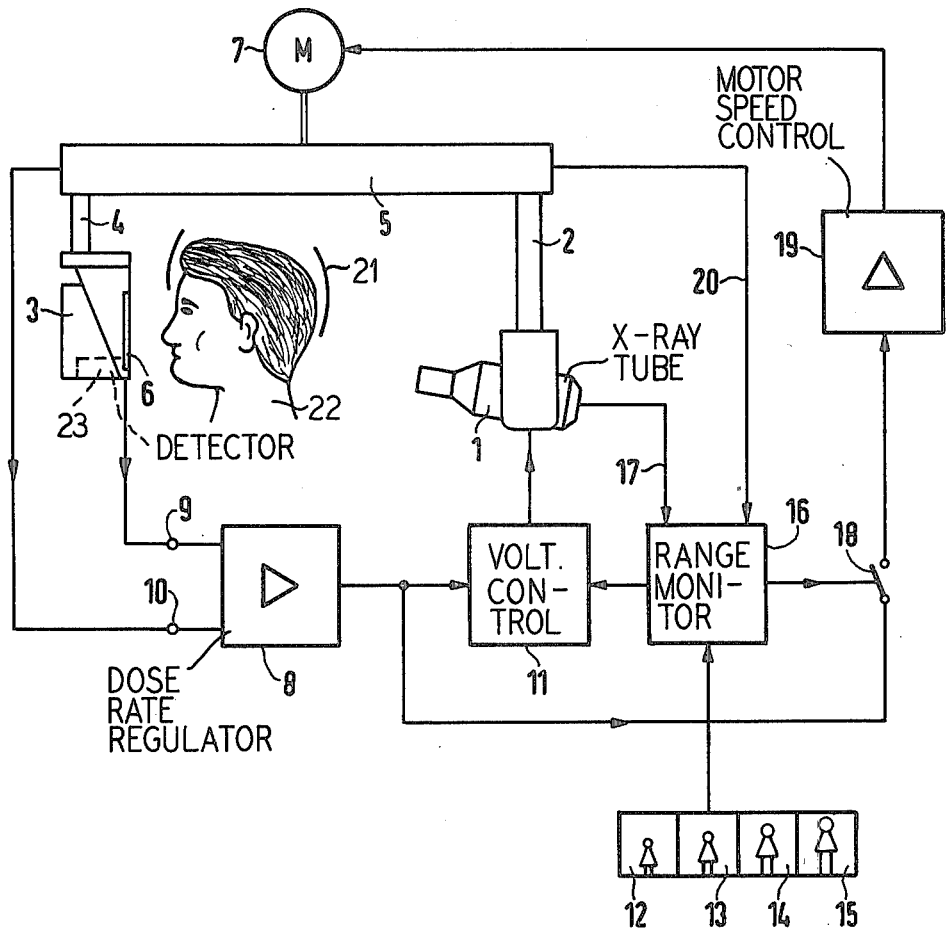

DENTAL X-RAY DIAGNOSTIC INSTALLATION

BACKGROUND OF THE INVENTION

1. Field of the Invention

The present invention relates to dental x-ray diagnostic installations and in particular to such installations having a means for controlling the radiation dose rate for obtaining an optimum film exposure.

2. Description of the Prior Art

An x-ray diagnostic installation is disclosed in German Pat. No. OS 24 47 075 which includes an x-ray tube and a cassette holder spaced therefrom which are rotatable about vertical axes around a patient's head for generating a dental x-ray of the patient's jaw and teeth. The cassette holder has a radiation detector attached thereto which generates an electrical signal corresponding to the radiation dose rate when struck by the x-rays. This electrical signal is supplied to a dose rate regulator which controls the x-ray tube voltage such that the dose rate is maintained at a level for producing an optimum film darkening or exposure.

Alternatively, the x-ray tube current may be controlled to achieve the same result. This conventional device operates on the principle that the x-ray tube voltage or current will be altered in accordance with the density characteristics of the patient in such a manner that the mean radiation dose reaching the individual film sections is maintained constant. The density characteristics of a patient may fluctuate greatly during the course of a sweep of the x-ray tube and cassette holder in the course of generating a total fluoroscopy. Additionally, relatively large differences in density characteristics are also observed between individual patients, for example between children and adults. Accordingly, the installation disclosed in German Pat. No. OS 24 47 075 requires a relatively large range of adjustment in order to maintain the radiation dose at a constant level.

SUMMARY OF THE INVENTION

It is an object of the present invention to provide a dental x-ray diagnostic installation which controls the radiation dose rate in order to achieve optimum film exposure by manipulating the x-ray tube voltage wherein the range within which the x-ray tube voltage is adjusted is relatively small.

The above object is inventively achieved in an x-ray diagnostic installation which has, in addition to a means for regulating the x-ray tube voltage, an additional dose regulating means for controlling the speed of movement of the exposure unit about the patient's head, or for controlling the x-ray tube current, whenever a specified range of adjustment for the x-ray tube voltage is exceeded. The result is that the x-ray tube voltage determining the fluoroscopy contrast deviates only slightly as a result of the regulation in order to achieve optimum exposure for a particular patient.

In the installation constructed in accordance with the principles of the present invention, a detector monitors whether the x-ray tube voltage is within a prescribed range and automatically causes the speed of movement of the exposure unit, and thus the speed of movement of the film, in order to maintian an optimum exposure level. The x-ray tube voltage can thus be matched to the characteristics of a particular patient. The range within which the x-ray tube voltage will be varied can be kept small so that the fluoroscopy contrast, dependent on the x-ray tube voltage, can be optimally obtained. The range within which the x-ray tube voltage may fluctuate can be individually determined by a selection means in accordance with characteristics of a particular patient.

BRIEF DESCRIPTION OF THE DRAWING

The single FIGURE shows a schematic representation of a dental x-ray diagnostic installation constructed in accordance with the principles of the present invention.

DESCRIPTION OF THE PREFERRED EMBODIMENTS

As shown in the drawing, an x-ray diagnostic installation constructed in accordance with the principles of the present invention has an x-ray tube 1 mounted on a height-adjustable support arm 2. X-ray film is secured to a cassette holder 3 in a semicircularly curved cassette. The cassette holder 3 is mounted on a support arm 4 and has a slit diaphragm 6 disposed in front of the cassette holder 3 as viewed in the direction of radiation. The support arms 2 and 4 are connected to a boom 5. The elements supported by the boom 5 comprise the exposure unit. The exposure unit is rotatable by a motor 7 about the head of a patient 22 which is held in place by a head support 21. The motor 7 also serves to advance the film in the film cassette.

As the exposure unit rotates, the x-ray tube 1 and the cassette holder 3 are rotated about vertical axes such that the x-rays always strike the patient's teeth at a right angle and a constant number of teeth per unit length of film is maintained. During rotation of the cassette holder 3 and the x-ray tube 1 around the head of the patient 22, the teeth, in succession, and the jaw of the patient are imaged on the film carried in the cassette holder 3. The cassette with the x-ray film is moved behind the slit diaphragm 6 with a perscribed velocity rate.

The x-ray tube 1 is supplied with high voltage and filament voltage in a known manner by the secondary winding of a high voltage transformer. In order to maintain the radiation dose operating on the individual sections of the x-ray film in the film cassette at a constant level, a radiation detector 23 is attached to the cassette holder 3, the radiation detector 23 generating an electrical signal corresponding to the actual value of the radiation dose rate. This signal is supplied to the input 9 of a dose rate regulator which also has an input 10 at which a signal corresponding to the film speed is supplied.

The dose rate regulator 8 operates a voltage control unit 11 so as to regulate the high voltage supplied to the x-ray tube 1 so as to maintain the radiation dose at a level for generating an optimum film exposure or darkening.

An optimum range for the x-ray tube voltage is selected by means of manually operable keys 12, 13, 14 and 15, each of which represents a voltage range corresponding to different patient characteristics. The selected voltage range is monitored by a range monitor 16 which receives a signal at an input 17 corresponding to the actual value of the x-ray tube voltage. As soon as the selected limit for the range of the x-ray tube voltage is reached, the monitoring circuit 16 closes an electronic switch 18 so that the output signal from the dose rate regulator 8 is supplied to a motor speed control unit 19 for regulating the speed of the motor 7 and thus the film speed. In this manner, instead of continuously increasing or decreasing the x-ray tube voltage over a wide adjustment range, the x-ray tube voltage is regulated only over a relatively small selected range and if conditions warrant a change in the radiation dose which would require an x-ray tube voltage greater than or less than the prescribed range, the same result is achieved by instead changing the film speed. Optimum exposure of the film is thus still achieved but the wide adjustment range for the x-ray tube voltage normally necessary in conventional installations is eliminated.

The range monitor 16 receives a signal at an input 20 corresponding to the speed of the motor 7 and will again open the switch 18 when this speed has been changed to such a degree that optimum exposure of the film can be achieved solely by control of the x-ray tube voltage.

The monitoring circuit 16 may also be utilized to control the x-ray tube current, instead of changing the speed of the motor 7, in order to maintain optimum film exposure when the x-ray tube voltage would otherwise be required to exceed the selected range. In general, the range monitor 16 can be utilized to regulate any non-voltage parameter affecting exposure of the film.

Although modifications and changes may be suggested by those skilled in the art it is the intention of the inventor to embody within the patent warranted hereon all changes and modifications as reasonably and properly come within the scope of his contribution to the art.

I claim as my invention:

1. A dental x-ray diagnostic installation comprising:
   an x-ray tube;
   a cassette holder for holding a cassette of x-ray film;
   a support means for supporting said x-ray tube and said cassette holder;
   a means for rotating said support means such that said x-ray tube and said cassette holder rotate about a patient's head, and for advancing said x-ray film in said cassette;
   a radiation detector attached to said cassette holder for generating an electrical signal corresponding to the radiation dose rate when struck by x-rays from said x-ray tube;
   a dose rate regulator connected to said radiation detector;
   a voltage control unit connected to said dose rate regulator and to said x-ray tube for setting the voltage level of said x-ray tube in response to a signal received from said dose rate regulator; and
   a range monitor for monitoring the x-ray tube voltage and for regulating a non-voltage parameter of said installation if said x-ray tube voltage is outside of a preselected voltage range such that optimum exposure of said film is maintained.

2. The dental x-ray diagnostic installation of claim 1 wherein said non-voltage parameter which is regulated by said range monitor is the speed of said film in said cassette.

3. The dental x-ray diagnostic installation of claim 1 wherein said non-voltage parameter regulated by said range monitor is the current supplied to said x-ray tube.

4. The dental x-ray diagnostic installation of claim 1 further comprising a means connected to said range monitor for permitting manual selection of said voltage range from a plurality of different voltage ranges adapted to different patient characteristics.

* * * * *